United States Patent
Giloh

(10) Patent No.: US 9,517,165 B2
(45) Date of Patent: Dec. 13, 2016

(54) METHOD AND APPARATUS TO TEMPORARILY RESTRAIN STRETCHABLE NON-WOVEN FABRIC

(75) Inventor: Ehud Giloh, Manchester (GB)

(73) Assignee: TamiCare Ltd., Heywood (GB)

(*) Notice: Subject to any disclaimer, the term of this patent is extended or adjusted under 35 U.S.C. 154(b) by 200 days.

(21) Appl. No.: 13/546,538

(22) Filed: Jul. 11, 2012

(65) Prior Publication Data

US 2013/0017747 A1 Jan. 17, 2013

Related U.S. Application Data

(60) Provisional application No. 61/508,317, filed on Jul. 15, 2011.

(51) Int. Cl.
| | | |
|---|---|---|
| *D04H 13/00* | (2006.01) | |
| *A61F 13/15* | (2006.01) | |
| *A61F 13/49* | (2006.01) | |
| *D04H 5/08* | (2012.01) | |

(52) U.S. Cl.
CPC ... *A61F 13/15707* (2013.01); *A61F 13/49009* (2013.01); *D04H 5/08* (2013.01); *Y10T 442/602* (2015.04)

(58) Field of Classification Search
CPC .............. D06M 7/00; A61F 13/15707; A61F 13/49009; Y10T 442/601; Y10T 442/602; D04H 5/08
USPC ................................... 28/104, 112
See application file for complete search history.

(56) References Cited

U.S. PATENT DOCUMENTS

| | | | | | |
|---|---|---|---|---|---|
| 2,903,387 | A | * | 9/1959 | Worth | 442/329 |
| 2,915,067 | A | * | 12/1959 | Bracht | 450/45 |
| 5,468,428 | A | * | 11/1995 | Hanschen et al. | 264/483 |
| 5,636,393 | A | * | 6/1997 | Zafiroglu et al. | 428/102 |
| 5,861,074 | A | * | 1/1999 | Wu | 156/229 |
| 6,204,207 | B1 | * | 3/2001 | Cederblad et al. | 442/5 |
| 6,541,403 | B2 | * | 4/2003 | Billarant et al. | 442/328 |
| 2006/0032578 | A1 | * | 2/2006 | Schneider | 428/212 |
| 2006/0135021 | A1 | * | 6/2006 | Calhoun et al. | 442/328 |
| 2006/0246803 | A1 | | 11/2006 | Smith et al. | |
| 2008/0182468 | A1 | | 7/2008 | Dharmarajan | |
| 2008/0292788 | A1 | | 11/2008 | Giloh | |

(Continued)

FOREIGN PATENT DOCUMENTS

| | | | | |
|---|---|---|---|---|
| EP | 477525 A1 * | 4/1992 | | D02G 3/32 |
| EP | 1 876 277 A1 | 1/2008 | | |

(Continued)

OTHER PUBLICATIONS

English abstract of JP 60-126376 A, published on Jul. 5, 1985, obtained from Derwent database.*

(Continued)

*Primary Examiner* — Jeremy R Pierce
(74) *Attorney, Agent, or Firm* — McDonnell Boehnen Hulbert & Berghoff LLP

(57) ABSTRACT

A method for obtaining temporary non-stretchability characteristics, mainly in a machine direction, in a non-woven fabric having any level of stretchability, in order to ease converting is disclosed. The non-stretchability characteristics can be then eliminated in order to restore the original characteristics of the non-woven fabric. This technique allows the formation of final products comprising stretchable non-woven fabrics by converting machines.

2 Claims, 2 Drawing Sheets

(56) References Cited

U.S. PATENT DOCUMENTS

2009/0047855 A1* 2/2009 Seth et al. ............... 442/329

FOREIGN PATENT DOCUMENTS

| JP | 60126376 A * | 7/1985 | ............ D06M 13/02 |
| JP | 60194174 A * | 10/1985 | ............ D06M 13/02 |
| WO | WO 2006/017518 A2 | 2/2006 | |
| WO | WO 2009/032867 A1 | 3/2009 | |

OTHER PUBLICATIONS

English abstract of JP 60-194174 A, published on Oct. 2, 1985, obtained from Derwent database.*
A computerized English translation of EP 0477525 B1, published on Aug. 16, 1991, obtained from European Patent Office's website.*
Full English translation to JP 60-194174 A, Mori, Oct. 1985.*
Full English translation to JP 60-126376 A, Mori, Jul. 1985.*

* cited by examiner

METHOD AND APPARATUS TO TEMPORARILY RESTRAIN STRETCHABLE NON-WOVEN FABRIC

CROSS-REFERENCE TO RELATED APPLICATIONS

The present application claims the benefit of priority to U.S. Provisional Application Ser. No. 61/508,317, filed on Jul. 15, 2011, the entire contents of which is incorporated by reference herein in its entirety.

BACKGROUND

Stretchable non-woven elastomeric fabrics are known in the art. One example of a stretchable non-woven material is described in US Patent Publication No. 2008/0292788, published Nov. 27, 2008.

U.S. Patent Publication No. 2008/0292788 also describes a method to produce the stretchable fabric on a conveyer belt apparatus, and to produce a sheet of the material to be further processed and converted from roll goods on converting machines, as commonly used in the non-woven industry.

A known issue in the industry is related to the production process of the roll goods on a converting machine, as the tension applied on the rolled material in the machine direction (MD) during the processing on the converting machines may create overstretching, deformation, or tearing of the material. When the non-woven material is stretchable, the problem becomes worse. This application discloses a solution to resolve this problem.

SUMMARY

The present application discloses a non-woven fabric with an ability to be temporarily non-stretchable, or to temporarily have limited stretchability. This ability can be implemented in any non-woven fabric having a level of elasticity, stretchability and/or resiliency.

In this disclosure, the terms elastic, stretchable, or resilient materials, are interchangeable.

The non-woven fabric may be made by any method, including but not limited to, the method disclosed in US Patent Publication No. 2008/0292788.

The current application discloses a product, manufacturing method, and related apparatuses.

Generally, the disclosure relates to obtaining temporary non-stretchability characteristics, mainly in the machine direction, in a non-woven fabric having any level of stretchability, in order to ease converting. The non-stretchability characteristics can be then eliminated in order to restore the original characteristics of the non-woven fabric. This technique allows the formation of final products comprising stretchable non-woven fabrics by converting machines.

For further clarification, while existing material can be stretched to a certain extent, the term 'non-stretchable' used in this disclosure relates to materials which are considered to be non-stretchable or can be stretched only by a few percentages.

DETAILED DESCRIPTION OF EMBODIMENTS OF THE INVENTION

The present disclosure relates to stretchability modification or transformation of any non-woven fabric in order to facilitate the running of a rolled non-woven fabric in a converting machine. The stretchability modification also prevents material deformation during the converting process.

The method of modifying the stretchability of the material includes at least two steps. First, stretchability of the non-woven sheet is temporarily restrained. Second, the non-stretchability characteristics of the non-woven sheet are eliminated, and the stretchability is restored.

The method may be implemented by a variety of embodiments. The following are some representative embodiments.

Figure 1:
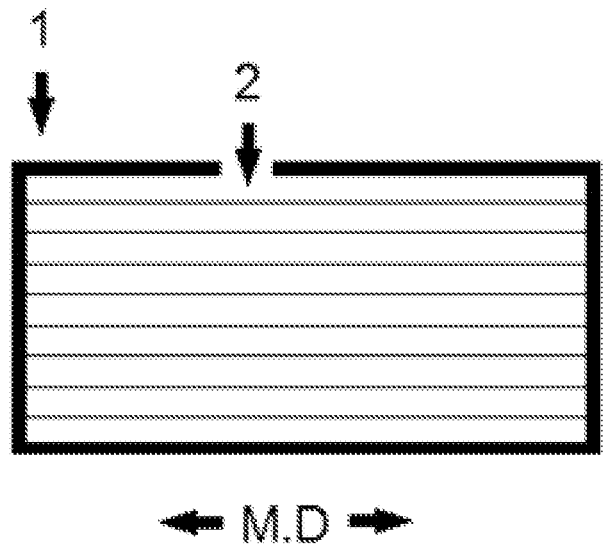
FIG. 1 shows a non-woven sheet associated with non-stretchable elements.

Referring to FIG. 1, a stretchable non-woven sheet or fabric 1 is associated with non-stretchable elements 2. Stretchability of the non-woven sheet 1 is temporarily restrained by attaching or embedding relatively non-stretchable components to the non-woven fabric 1, such as strings or long fibers, to create the non-stretchable elements 2.

The strings or long fibers are associated with the non-woven fabric 1 in such a way that a non-stretchability feature is created in at least the machine direction, (which is longitudinal to the roll direction).

The non-stretchable elements 2 can be made out of any suitable material such as, but not limited to, metal, cotton, viscose, paper, polyester, polyethylene, polypropylene, any polymer, or any other suitable relatively non-stretchable material in comparison to the stretchability of the rolled sheet.

The non-stretchable elements 2 can be created by any suitable method, or can be inserted, for instance, by stitching the non-stretchable components to the stretchable non-woven fabric during or after the production of the stretchable non-woven fabric.

In another embodiment, the non-stretchable elements 2 are created by applying manipulations on the non-woven fabric materials, such as by creating denser area of fibers by melting or gluing the fibers, by thermo-bonding, or by any other suitable method. Alternatively, the non-stretchable elements 2 may be created by embedding non-stretchable components, such as strings or long fibers, into the stretchable non-woven fabric 1 during the manufacturing process. The non-stretchable components may be placed inside the stretchable non-woven fabric 1, between layers creating the stretchable non-woven fabric, or between layers of elastomeric materials forming the stretchable non-woven fabric. The non-stretchable components are associated with the stretchable material in at least the machine direction to allow smooth and even running during the converting process.

In yet another embodiment, the non-stretchable elements 2 may be associated with the non-woven fabric 1 during the application of a liquid elastomeric material layer, or between steps of layers application. Layers of elastomeric material liquid may be applied on a wall, mold, workpiece former, conveyor belt, or a workpiece former that is linked to a conveyor. The application of the liquid elastomeric material can be made by spraying, brushing, lamination or by any other suitable way, so that when the liquid elastomeric material layer cures, the non-stretchable elements 2 are already embedded into the non-woven fabric 1.

In the case of non-woven fabric based on liquid elastomeric materials, such as synthetic rubber or natural rubber, the non-stretchable elements 2 may be associated with the stretchable non-woven sheet 1 after curing of the liquid elastomeric material and prior to the rolling of the stretchable non-woven fabric.

In yet another embodiment, the non-stretchable elements 2 may be a sheet or mesh associated with the stretchable non-woven fabric 1 by attaching and rolling the elements 2 and the fabric 1 together. The sheet or mesh can be made out of any suitable non-stretchable material, such as, but not limited to, metal, cotton, viscose, paper, polyester, polyethylene, polypropylene, any polymer, or any other suitable material. The associating of the non-stretchable sheet or mesh with the stretchable non-woven sheet can be executed during the manufacturing process of the stretchable non-woven fabric 1, or after the manufacturing process of the stretchable non-woven fabric so that the non-stretchable sheet or mesh prevents the stretchable non-woven sheet from being stretched during the converting process, allowing smooth and trouble-free converting.

The method of the present application further includes elimination or removal of the non-stretchability characteristics that have been acquired by the stretchable non-woven fabric during the first step, so the original resiliency of the fabric 1 is resumed and regained.

In one embodiment, the non-stretchability characteristics are eliminated by breaking the continuity of the components that make up the non-stretchable elements 2, such as strings, long fibres, or mesh, during processing in a converting machine. Breaking the continuity of the non-stretchable elements (strings, long fibres or mesh), can be implemented on the converting machine by cutting the non-stretchable elements at a desired pitch. The pitch may vary typically between less than a few millimeters to more than a few centimeters. The cutting may be executed by any means or device, such as, but not limited to, a mechanical punch, water jet, laser or other electromagnetic radiation, chemical reaction, melting, or by any other suitable means known in the art.

After breaking the continuity of the non-stretchable components (strings, fibres, or mesh), the non-stretchable components appear in form of short segments 3 (shown in FIG. 2) according to the breaking pitch.

Figure 2:
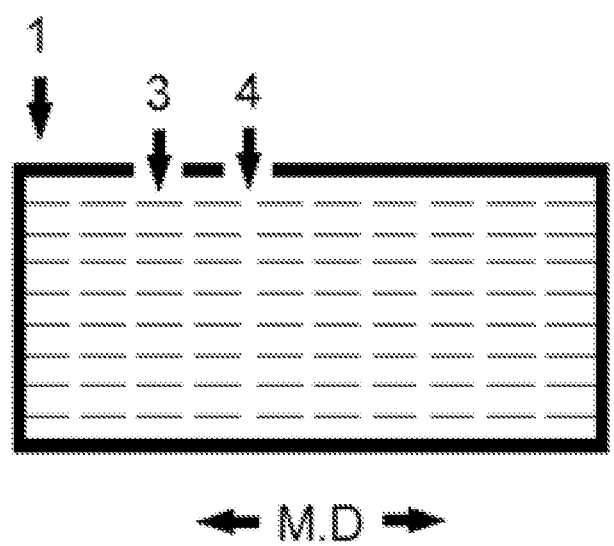
FIG. 2 shows the non-woven sheet of FIG. 1 after breaking the continuity of the non-stretchable elements.

FIG. 2 shows the non-woven sheet 1 after breaking the continuity of the non-stretchable elements, showing the remaining shorter non-stretchable elements 3, and a small gap 4 between the remaining elements created at points where the breaking occurred. In another embodiment, the non-stretchable sheet or mesh is removed from the stretchable sheet by separating the non-stretchable sheet from the stretchable non-woven fabric 1 during the converting process. The non-stretchable sheet or mesh may be rolled and reused.

Figure 3:
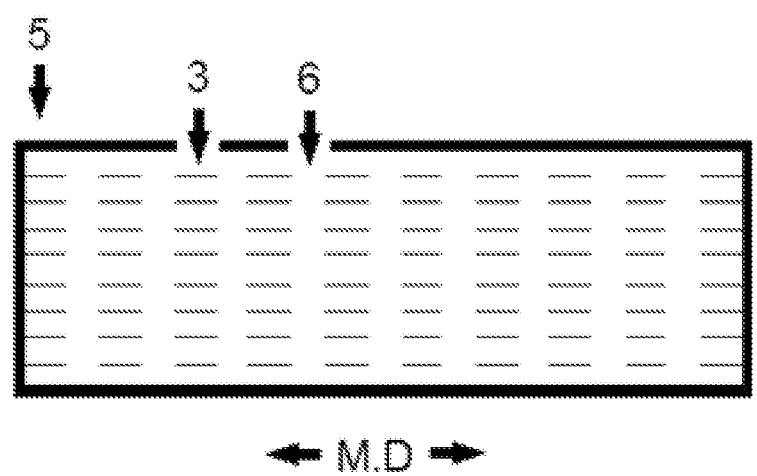
FIG. 3 shows the non-woven sheet after being stretched.

FIG. 3 shows the stretched non-woven sheet 5. The remaining non-stretchable elements 3 are present in the non-woven fabric, while gaps 6 between the remaining non-stretchable elements 3 are larger than the small gaps 4 as a result of the stretching of the fabric.

By eliminating the non-stretchability characteristics of the stretchable non-woven fabric, the strings or long fibers are still connected to or embedded into the stretchable fabric 1, but are cut to short segments 3, and therefore cannot restrain the stretchability of the fabric. The fabric has now regained its previous stretchability and resiliency, thus allowing the smooth and trouble free production of stretchable final products on a converting machine.

It is preferred that the material of the non-stretchable elements will have low adherent to the materials creating the web of the stretchable non-woven fabric. This allows the short segments 3 to be movable within the non-woven fabric 1.

The short segments 3 will not stay bonded to the stretchable non-woven materials; they are movable inside the non-woven fabric web. In other words, the friction between the non-stretchable elements and the stretchable non-woven fabric allows the short segments 3 to move freely in the fabric after being cut.

After the continuity of the non-stretchable elements 2 is eliminated, for instance by breaking or cutting the strings or the long fibres, the cut, short segments of the non-stretchable elements are not connected anymore and do not hold the non-woven fabric. The short segments 3 are "floating" within the stretchable non-woven fabric 1, at various locations, such that the stretchable non-woven fabric is not restrained anymore. The gap or distance 6 between each segment becomes wider when the fabric is stretched.

The apparatus of the present application includes two sections or devices. The first device creates or associates the non-stretchable elements 2, in the form of strings, long fibres, mesh, or any other suitable non-stretchable element to the stretchable non-woven sheet, during the production of the stretchable non-woven fabric or after the production of the stretchable non-woven fabric. The second device is mounted on the converting machine to execute the elimination of the non-stretchability of the non-woven fabric.

The first device of the apparatus is associated with the machine that manufactures the sheet or the roll of the stretchable non-woven fabric.

The second device of the apparatus is associated with the converting machine and executes the step of eliminating the previously added non-stretchability characteristics by breaking the continuity of the non-stretchable components (such as strings, long fibres or mesh), during the processing or the dispensing in the converting machine. Breaking the continuity of the non-stretchable components can be implemented on the converting machine by cutting them at any suitable pitch. The pitch may vary between a few millimeters or less, to a few centimeters or more. The cutting may be implemented using any means or device, such as, but not limited to, mechanical punch, water jet, electromagnetic radiation, chemical reaction or melting or by any other suitable means known in the art.

I claim:

1. A method to temporarily restrain stretchability of a stretchable non-woven fabric during a converting process, said method comprising:
   (a) providing a stretchable non-woven fabric;
   (b) modifying the stretchable non-woven fabric by inserting non-stretchable elements, the non-stretchable elements consisting of a continuous string or fiber, into the stretchable non-woven fabric to provide non-stretchability characteristics to the stretchable non-woven fabric so as to temporarily restrain stretchability of the non-woven fabric at least in the machine direction; and
   (c) restoring the stretchability of the stretchable non-woven fabric by subsequently eliminating the non-stretchability characteristics previously acquired by the non-woven fabric by eliminating continuity of the non-stretchable elements by disconnecting, cutting, or melting the non-stretchable elements into short segments during or after a converting process, wherein the short segments are not bonded to the non-woven fabric and move freely within the non-woven fabric, and wherein the short segments do not restrain the stretchability of the non-woven fabric.

2. A method to temporarily restrain stretchability of a stretchable non-woven fabric during a converting process, said method comprising:
- (a) providing a stretchable non-woven fabric;
- (b) modifying the stretchable non-woven fabric by temporarily creating non-stretchable elements in the stretchable non-woven fabric to provide non-stretchability characteristics in the stretchable non-woven fabric so as to temporarily restrain stretchability of the non-woven fabric at least in the machine direction, wherein the non-stretchable elements are created by melting or thermo-bonding the non-woven fabric to create a dense area of fibers within the non-woven fabric; and
- (c) restoring the stretchability of the stretchable non-woven fabric by subsequently eliminating the non-stretchability characteristics previously acquired by the non-woven fabric by eliminating the non-stretchable elements during or after a converting process.

\* \* \* \* \*